(12) United States Patent
Lester, Jr. et al.

(10) Patent No.: US 7,981,822 B2
(45) Date of Patent: Jul. 19, 2011

(54) HOOK AND LOOP FASTENER DEVICE

(75) Inventors: Donald H. Lester, Jr., Waxhaw, NC (US); David L. Lunceford, Kingsport, TN (US)

(73) Assignee: Aplix S.A., Paris (FR)

( * ) Notice: Subject to any disclaimer, the term of this patent is extended or adjusted under 35 U.S.C. 154(b) by 900 days.

(21) Appl. No.: 11/178,906

(22) Filed: Jul. 11, 2005

(65) Prior Publication Data
US 2006/0019572 A1     Jan. 26, 2006

Related U.S. Application Data

(63) Continuation-in-part of application No. 10/896,220, filed on Jul. 21, 2004, now abandoned.

(51) Int. Cl.
*D04H 1/58* (2006.01)
*D04H 1/60* (2006.01)
*D04H 1/62* (2006.01)

(52) U.S. Cl. ........ 442/411; 442/361; 442/409; 442/415; 428/212; 428/218

(58) Field of Classification Search .......... 442/361–365, 442/409, 411, 415, 402, 403, 407, 408; 428/212, 428/218
See application file for complete search history.

(56) References Cited

U.S. PATENT DOCUMENTS

| | | | |
|---|---|---|---|
| 4,018,646 A * | 4/1977 | Ruffo et al. | 162/146 |
| 4,373,000 A * | 2/1983 | Knoke et al. | 428/198 |
| 4,542,060 A * | 9/1985 | Yoshida et al. | 442/389 |
| 5,079,074 A * | 1/1992 | Steagall et al. | 428/218 |
| 5,326,612 A | 7/1994 | Goulait | |
| 5,616,394 A | 4/1997 | Gorman et al. | |
| 5,667,619 A * | 9/1997 | Alikhan | 156/253 |
| 5,773,120 A | 6/1998 | Deka et al. | |
| 5,786,060 A | 7/1998 | Takahashi et al. | |
| 5,841,081 A * | 11/1998 | Thompson et al. | 181/286 |
| 5,858,515 A | 1/1999 | Stokes et al. | |
| 5,888,607 A | 3/1999 | Seth et al. | |
| 5,997,981 A * | 12/1999 | McCormack et al. | 428/99 |
| 6,048,809 A * | 4/2000 | Brow et al. | 442/364 |
| 6,218,593 B1 | 4/2001 | Torimae et al. | |
| 6,589,638 B1 * | 7/2003 | McCormack et al. | 428/198 |
| 6,955,847 B1 * | 10/2005 | Itou et al. | 428/174 |
| 2005/0191460 A1 * | 9/2005 | Belau | 428/103 |

OTHER PUBLICATIONS

Kosa, "Various Fiber Definitions," Dictionary of Fiber & Textile Technology, 7th ed., KoSa (Charlotte, NC), (Dec. 21, 1999).

* cited by examiner

*Primary Examiner* — Jenna-Leigh Johnson
(74) *Attorney, Agent, or Firm* — Hammer & Associates, P.C.

(57) ABSTRACT

The instant invention is a hook and loop fastener device. According to the instant invention, the hook and loop fastener device includes a loop component. The loop component includes a binder-free non-woven material having a bottom layer and a top layer. The bottom layer includes a first bicomponent fiber and a first monocomponent fiber. The first bicomponent fiber comprises the majority of the bottom layer based on total weight of the bottom layer, and the first monocomponent fiber comprises the balance thereof. The top layer includes a second bicomponent fiber, and a second monocomponent fiber. The second monocomponent fiber comprises the majority of the top layer based on total weight of the top layer, and the second bicomponent layer comprises the balance thereof. The bottom layer and the top layer may further include interfiber bonding to form the binder-free non-woven material. The non-woven material may further be island bonded via hot-roll calendering thereby forming a bonded area and a non-bonded area. Additionally, the loop component may include a backing layer bonded to the non-woven material.

26 Claims, 9 Drawing Sheets

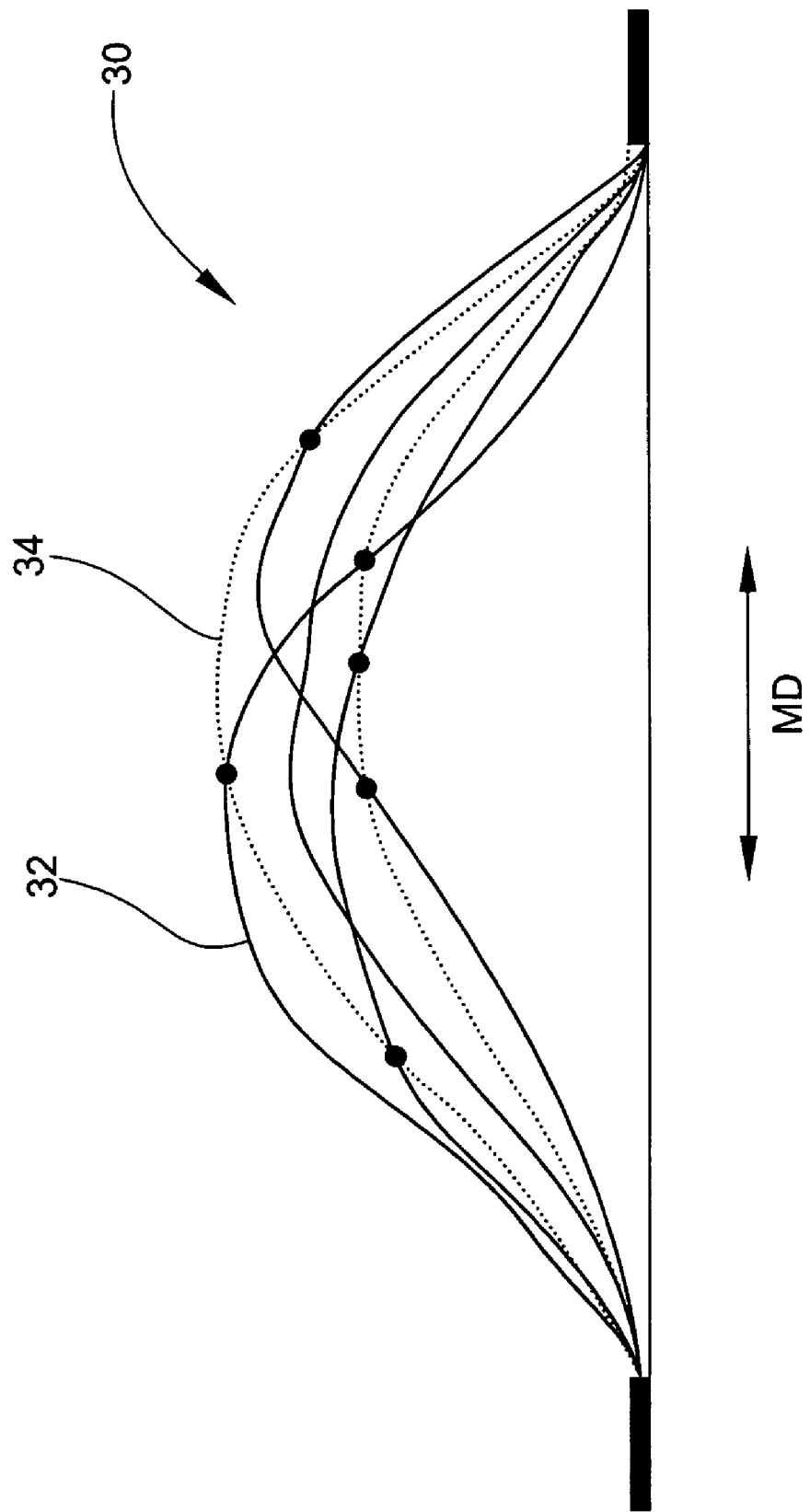

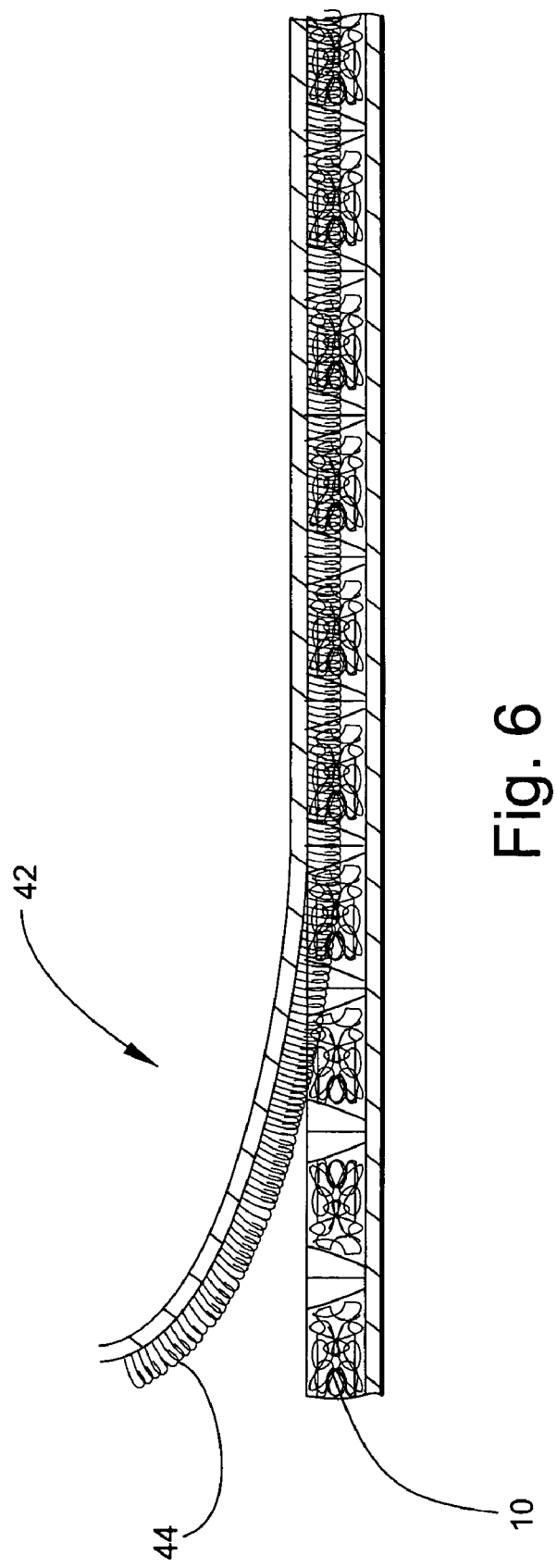

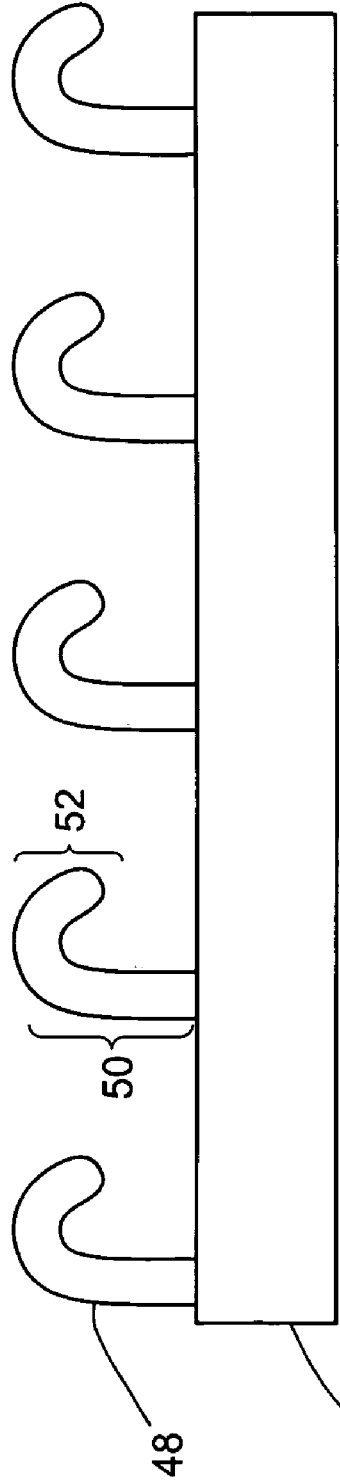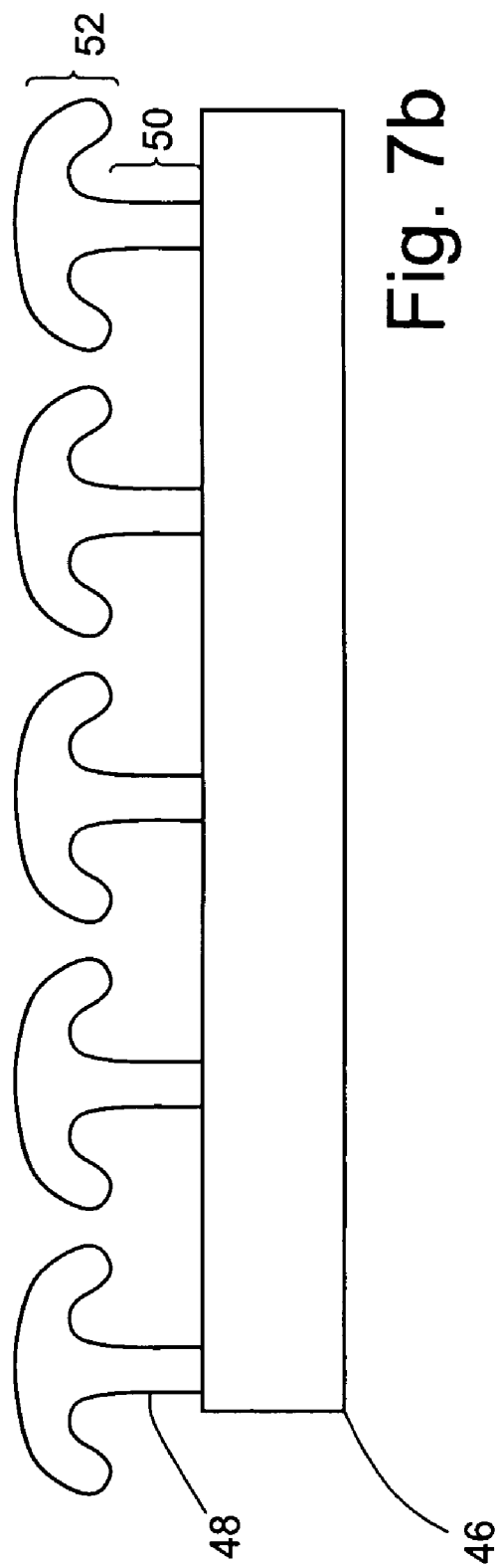

HOOK AND LOOP FASTENER DEVICE

CROSS-REFERENCE TO RELATED APPLICATIONS

This application is a continuation-in-part of U.S. patent application Ser. No. 10/896,220 filed Jul. 21, 2004, now abandoned.

FIELD OF INVENTION

The instant invention relates to a hook and loop fastener device.

BACKGROUND OF THE INVENTION

The use of hook and loop fastener devices in consumer and industrial applications is widely known. Examples of such applications include disposable hygiene absorbent articles such as diapers, disposable garments such as surgical gowns, and the like.

In general, a hook and loop fastener device comprises a hook component and a loop component. The hook component includes a plurality of hook-shaped members anchored to a base material. The loop component includes a plurality of upstanding loop members projecting outwardly from a backing material. The hook-shaped members are designed to engage the loop members in order to provide a strong mechanical bond therebetween. The hook members and the loop members can typically be engaged and disengaged repeatedly.

However, when the hook and loop fastener device is intended to be used in a disposable hygiene absorbent article or a disposable garment, a low cost loop component, which adequately functions to provide a resealable mechanical closure for a limited number of applications, is desirable. There is no need for the loop component of a disposable article to possess long term capability for repetitious engagements and disengagement with the hook component because such articles only have a short life span. However, the loop component used in conjunction with the hook component should provide a relatively high peel strength, and a relatively high shear strength, i.e. it should secure closure for a limited number of use cycles. The use of non-woven material to provide a low cost loop component, which adequately functions to provide a resealable mechanical closure for a limited number of applications, is well known.

U.S. Pat. No. 5,326,612 discloses a female loop component, which includes a non-woven secured to a backing, for engaging a complementary hook component in a refastenable fastening device.

U.S. Pat. No. 5,616,394 discloses a sheet of loops, which includes a sheet of longitudinally oriented fibers having anchor portions and arcuate portions projecting in one direction away from the anchor portions, and a thermoplastic backing material.

U.S. Pat. No. 5,773,120 discloses a loop material, which includes a bonded carded web that contains a binder, suitable for use in a hook and loop fastening system.

U.S. Pat. No. 5,786,060 discloses a female member, which includes a web having a heat-melt-adhering composite fiber body. The web has loops formed on its first surface while its second surface is densely heat-melt-adhered together.

U.S. Pat. No. 5,858,515 discloses a pattern-unbonded non-woven fabric having continuous bonded areas defining a plurality of discrete unbonded area, which is suitable for use as a loop fastening material for hook and loop fastening systems.

U.S. Pat. No. 5,888,607 discloses a non-woven fibrous loop material, which contains an open fibrous loop layer comprised predominately of polypropylene polymer, copolymer, or blend fibers, for use in hook and loop fastening systems.

U.S. Pat. No. 6,218,593 discloses an absorbent article, which includes a top sheet, a back sheet, and an absorbent member interposed between the top sheet and the back sheet. The absorbent article includes a fastening member, which is formed of a male sheet member designed to be brought into direct contact with the surface of the non-woven fabric constituting a back sheet to form a mechanical bond therebetween.

When a hook and loop fastener device is intended to be used in disposable articles such as a disposable garment or a disposable hygiene absorbent article, different factors, i.e. fastening performance, texture, and aesthetics, must be considered with regard to the loop component. Fastening performance factors include peel strength as well as shear strength. A relatively high peel strength and shear strength is desired to secure closure for at least a limited number of use cycles without excessive fiber fuzz formation. Fuzz formation can occur when fibers break or pull free from the loop component upon disengagement with the hook component. Loop component texture factors include softness, flexibility, and resiliency, i.e. compression resistance. Softness and flexibility are important to avoid discomfort to the wearer, as well as providing a comfortable form-fitting garment or article. A relatively high degree of compression resistance, resolves problems, i.e. compression of the loop fibers, caused during the transportation and storage of loop materials. A high compression resistance is desirable because compression of the loop fibers impairs the optimum engagement between the hook members and the loop fibers; thus, the hook and loop fastening device fails to provide a secured closure. Finally, an aesthetic factor includes the visibility of printed graphics of the loop component to enhance the physical appearance of a hook and loop fastening device.

Despite the extensive levels of activity and research efforts in developing non-woven loop materials suitable for a limited number of application cycles, there is a still a need for a light weight, low cost, high performance loop material, which is relatively easy to manufacture, and possesses a relatively high degree of softness, compression resistance, and visibility of printed graphics, with additionally having the ability to be bonded to a further layer. Such loop material is suitable for a hook and loop fastener device, particularly as such as are used in disposable hygiene absorbent articles, e.g. diapers.

SUMMARY OF THE INVENTION

The instant invention is a hook and loop fastener device. According to the instant invention, the hook and loop fastener device includes a loop component. The loop component includes a binder-free non-woven material having a bottom layer and a top layer. The bottom layer includes a first bicomponent fiber and a first monocomponent fiber. The first bicomponent fiber comprises the majority of the bottom layer based on total weight of the bottom layer, and the first monocomponent fiber comprises the balance thereof. The top layer includes a second bicomponent fiber, and a second monocomponent fiber. The second monocomponent fiber comprises the majority of the top layer based on total weight of the top layer, and the second bicomponent layer comprises the balance thereof. The bottom layer and the top layer may further include interfiber bonding to form the binder-free non-woven material. The non-woven material may further be island bonded via hot-roll calendering thereby forming a bonded area and a non-bonded area. Additionally, the loop component may include a backing layer bonded to the non-woven material.

BRIEF DESCRIPTION OF THE DRAWINGS

For the purpose of illustrating the invention, there is shown in the drawings a form that is presently preferred; it being understood, however, that this invention is not limited to the precise arrangements and instrumentalities shown.

FIG. 4 is an enlarged sectional view of the top layer of the loop component shown in FIG. 1;

FIG. 6 is a cross-sectional view of a hook and loop fastener device;

FIGS. 7a and b are schematic illustrations of different hook shapes;

DETAILED DESCRIPTION OF THE INVENTION

Figure 1:
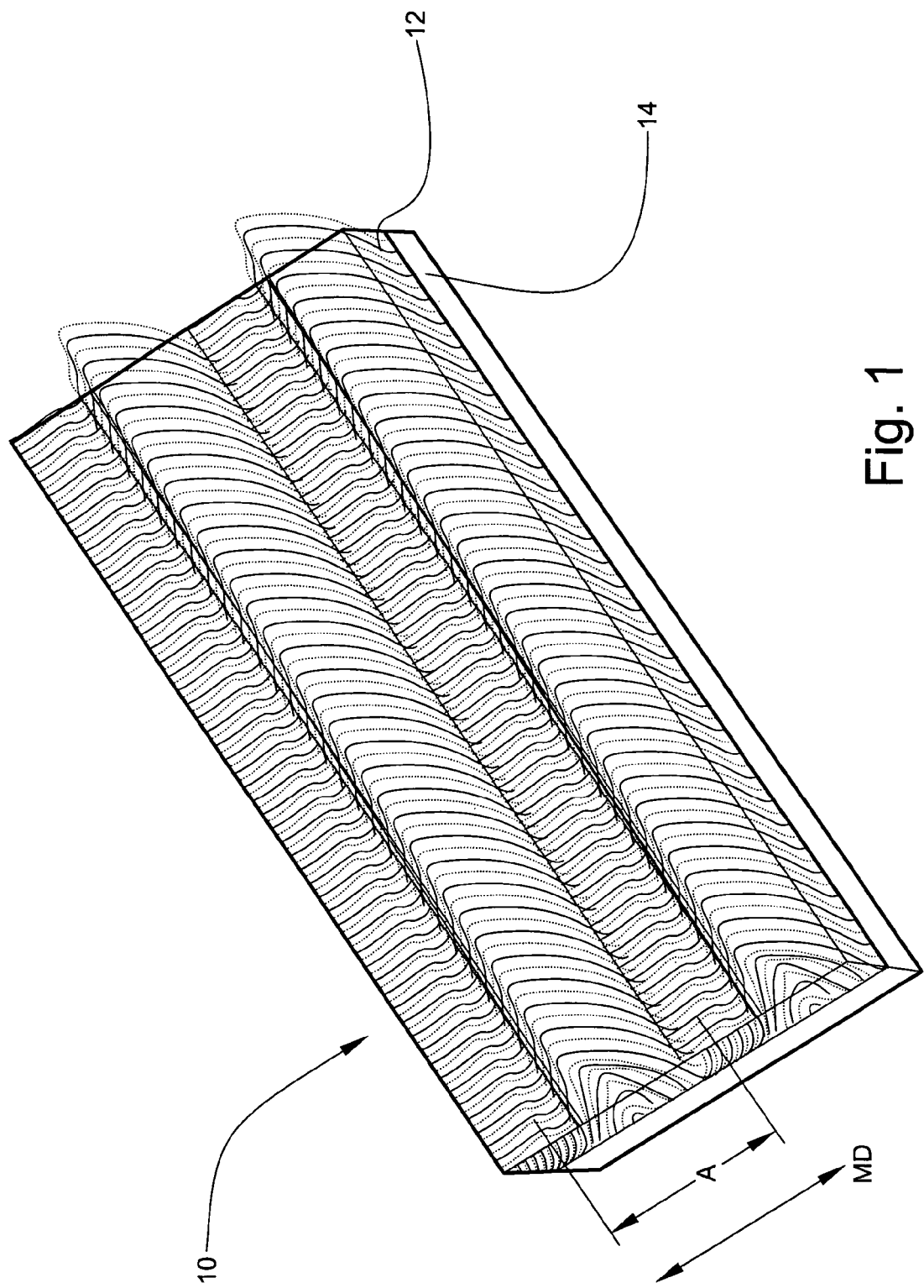
FIG. 1 is a perspective view of a loop component of the instant invention.
Figure 2:
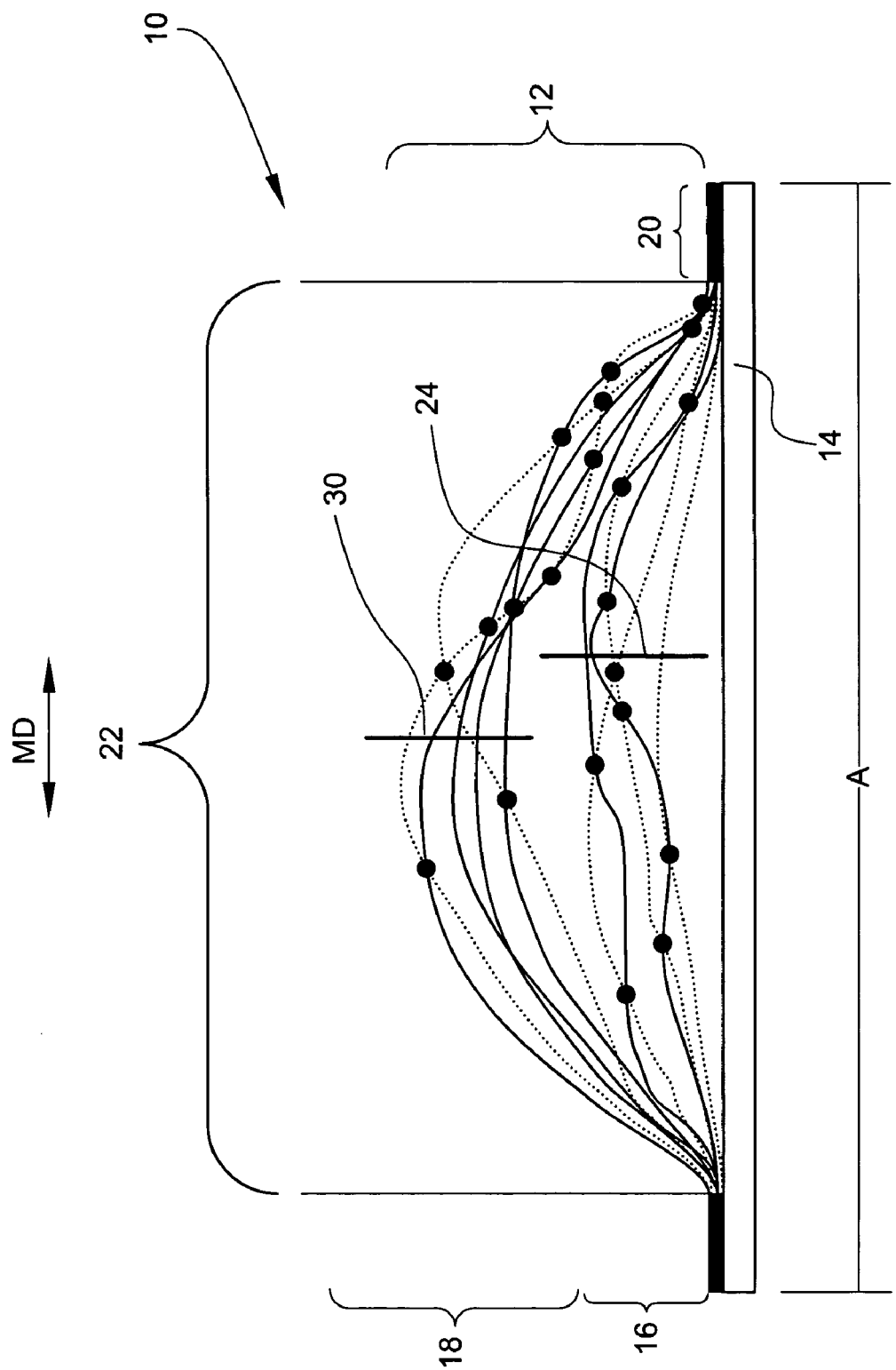
FIG. 2 is an enlarged sectional view of the loop component shown in FIG. 1.

Referring to the drawings wherein like numerals indicate like elements, there is shown, in FIG. 1, a preferred embodiment of a loop component 10. Loop component 10 includes a binder-free non-woven 12, and preferably, a backing layer 14. Non-woven 12 is a multi-layer carded non-woven. Preferably, non-woven 12 has at least two layers, a bottom layer 16 and a top layer 18, as shown in FIG. 2, but is not so limited. The instant invention will be discussed as having two layers herein.

Non-woven 12 may have a basis weight of 20 to 50 $g/m^2$, and preferably, non-woven 12 has a basis weight of 30 to 37 $g/m^2$. Non-woven 12 may have any thickness, and preferably, non-woven 12 has a thickness in the range of 40 to 90 mils (1.0 to 2.3 mm). Most preferably, non-woven 12 has a thickness of about 60 mils (1.5 mm). Furthermore, non-woven 12 may have any machine direction tensile strength. Preferably, non-woven 12 has a machine direction tensile strength of more than 450 g/2.54 cm. Most preferably, non-woven 12 has a machine direction tensile strength of 980 g/2.54 cm. In addition, non-woven 12 may have any cross-machine direction tensile strength. Preferably, non-woven 12 has a cross-machine direction tensile strength of at least 50 g/2.54 cm. Most preferably, non-woven 12 has a cross-machine direction tensile strength of 120 g/2.54 cm. Finally, non-woven 12 may have any density, and more preferably, non-woven 12 has a low density. Most preferably, the bottom layer 16 of the non-woven 12 has a greater density than the top layer 18 of non-woven 12.

Backing layer 14 may be positioned beneath the non-woven 12 to provide a foundation for the non-woven 12, and to provide dimensional stability. Backing layer serves as a surface to which the non-woven 12 can be affixed, and a surface on which graphics can be printed. Many types of materials are suitable for use as backing layer 14. The backing layer 14 preferably should be some type of material that the hook members of a hook component will not penetrate. The backing layer 14 may be a film, a non-woven web, or a woven fabric. Preferably, backing layer 14 is a film, as shown in FIG. 1. The backing layer may be made of any material, e.g. any polymer. For example, the backing layer 14 may be made of polyester, polyethylene, polypropylene, blends thereof, layers thereof, or any other suitable material. More preferably, the backing layer is made of any material, which is similar in chemistry to the first bicomponent fiber in order to provide stronger bonding therebetween. Furthermore, the backing layer 14 may have any thickness. Preferably, backing layer 14 has a thickness in the range of 9 to 28µ. In addition, the backing layer 14 may have any basis weight, and preferably, the backing layer 14 has a basis weight in the range of 10 to 30 $g/m^2$. Most preferably, the backing layer 14 has a basis weight in the range of 14 to 24 $g/m^2$. The backing layer 14 may be bonded to non-woven 12, as discussed below in further detail.

Backing layer 14 may be printed with a wide variety of printing inks using a wide variety of printing processes. Both the printing inks and printing processes may themselves be conventional. Furthermore, a wide variety of graphics may be printed on the backing layer 14, examples include, but are not limited to, patterns, designs, photographs, drawings, barcodes, words, ideas, concepts, logos, brands, trademarks, slogans, advertisings, instructions, cartoon characters and combinations thereof. In the alternative, where no backing layer is present, non-woven 12 may be printed with a wide variety of printing inks using a wide variety of printing processes. Both the printing inks and printing processes may themselves be conventional, as mentioned hereinabove. Furthermore, a wide variety of graphics may be printed on the non-woven 12, examples, as mentioned hereinabove, include, but are not limited to, patterns, designs, photographs, drawings, barcodes, words, ideas, concepts, logos, brands, trademarks, slogans, advertisings, instructions, cartoon characters and combinations thereof.

When the backing layer is present, the total basis weight of the non-woven 12 together with the backing layer 14 may be any basis weight. Preferably, the total basis weight of the non-woven 12 and backing layer 14 is in a range of 30 to 80 $g/m^2$. More preferably, the total basis weight of the non-woven 12 and backing layer 14 is in a range of 44 to 61 $g/m^2$.

Non-woven 12 may be translucent. Preferably, non-woven 12 is relatively highly translucent. Translucency of the non-woven 12 is important because a relatively high degree of translucency would ensure visibility of the printed graphics. However, translucency is inversely related to the basis weight of the non-woven 12, i.e. the lower the basis weight of the non-woven 12, the higher degree of translucency; therefore, both translucency of non-woven 12 and basis weight of non-woven 12 must be considered in tandem.

Figure 3:
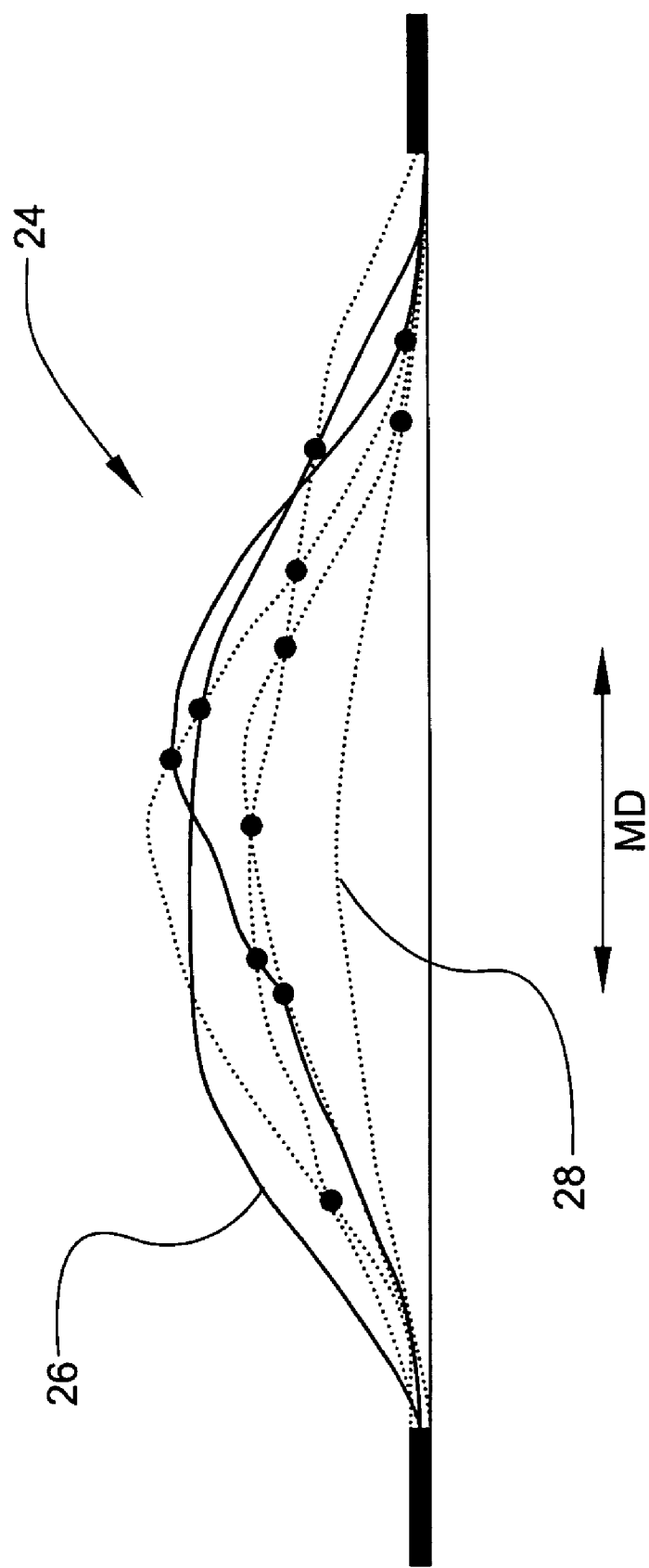
FIG. 3 is an enlarged sectional view of the bottom layer of the loop component shown in FIG. 1.

Referring to FIGS. 2 and 3, bottom layer 16, a non-woven strength layer, comprises a first fiber blend 24. Bottom layer 16 provides strength and a foundation to which the top layer 18 is bonded. First fiber blend 24 includes a first monocomponent fiber 26 and a first bicomponent fiber 28. Preferably, first fiber blend 24 includes a plurality of the first monocomponent fibers 26 and a plurality of the first bicomponent fibers 28. First bicomponent fibers 28 may comprise the majority of the first fiber blend 24 based on the total weight of the first fiber blend 24, and first monocomponent fiber 26 comprises the balance thereof. Preferably, first bicomponent fibers 28 comprise from about 60 to 99 percent by weight of the first fiber blend 24, and first monocomponent fiber 26 comprises the balance thereof, i.e. 1 to 40 percent by weight of the first fiber blend 24. More preferably, first bicomponent fibers 28 comprise from about 60 to 90 percent by weight of the first fiber blend 24, and first monocomponent fiber 26 comprises the balance thereof, i.e. 10 to 40 percent by weight of the first fiber blend 24. Most preferably, first bicomponent fibers 28 comprise about 90 percent by weight of the first fiber blend 24, and first monocomponent fiber 26 comprises the balance thereof, i.e. about 10 percent by weight of the first fiber blend 24.

Referring to FIGS. 2 and 4, top layer 18, a non-woven loop fastener layer, comprises a second fiber blend 30. Second fiber blend 30 includes a second monocomponent fiber 32 and a second bicomponent fiber 34. Preferably, second fiber blend 30 includes a plurality of the second monocomponent fibers 32 and a plurality of the second bicomponent fibers 34. Second monocomponent fibers 32 may comprise the majority of the second fiber blend 30 based on the total weight of the second fiber blend 30, and second bicomponent fiber 34 comprises the balance thereof. Preferably, second monocomponent fibers 32 comprise from about 60 to 99 percent by weight of the second fiber blend 30, and second bicomponent fiber 34 comprises the balance thereof, i.e. 1 to 40 percent by weight of the second blend 30. More preferably, second monocomponent fibers 32 comprise from about 60 to 85 percent by weight of the second fiber blend 30, and second bicomponent fiber 34 comprises the balance thereof, i.e. 15 to 40 percent by weight of the second blend 30. Most preferably, second monocomponent fibers 32 comprise about 80 percent by weight of the second fiber blend 30, and second bicomponent fiber 34 comprises the balance thereof, i.e. about 20 percent by weight of the second blend 30.

The first monocomponent fiber 26 of the bottom layer may be a thermoplastic polymer. Thermoplastic polymer, as used herein, refers to a polymer that melts when exposed to heat and returns to its original condition when cooled to room temperature. Examples of thermoplastic polymers include, by way of illustration only, end-capped polyacetals, such as poly(oxymethylene) or polyformaldehyde, poly(trichloroacetaldehyde), poly(n-valeraldehyde), poly(acetaldehyde), and poly(propionaldehyde); acrylic polymers, such as polyacrylamide, poly(acrylic acid), poly(methacrylic acid), poly(ethyl acrylate), and poly(methyl methacrylate); fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), and poly(vinyl fluoride); polyamides, such as poly(6-aminocaproic acid) or poly(e-caprolactam), poly(hexamethylene adipamide), poly(hexamethylene sebacamide), and poly(1 1-aminoundecanoic acid); polyaramides, such as poly(imino-1,3-phenyleneiminoisophthaloyl) or poly(m-phenylene isophthalamide); parylenes, such as poly-p-xylylene and poly (chloro-p-xylylene); polyaryl ethers, such as poly(oxy-2,6-dimethyl-1,4-phenylene) or poly(p-phenylene oxide); polyaryl sulfones, such as poly(oxy-1,4-phenylenesulfonyl-1,4-phenyleneoxy-1,4-phenylene-isopropylidene-1,4-phenylene)-and poly(sulfonyl-1,4-phenyleneoxy-1,4-phenylenesulfonyl-4,4'-biphenylene); polycarbonates, such as poly(bisphenol A) or poly(carbonyidioxy-1,4-phenyleneisopropylidene-1,4-phenylene); polyesters, such as poly (ethylene terephthalate), poly(tetramethylene terephthalate), and poly(cyclohexylene-1,4-dimethylene terephthalate) or poly(oxymethylene-1,4-cyclohexylenemethyleneoxyterephthaloyl); polyaryl sulfides, such as poly(phenylene sulfide) or poly(thio-1,4-phenylene); polyimides, such as poly (pyromellitimido-1,4-phenylene); polyolefins, such as polyethylene, polypropylene, poly(1-butene), poly(2-butene), poly(1-pentene), poly(2-pentene), poly(3-methyl-1-pentene), and poly(4-methyl-1-pentene); vinyl polymers, such as poly(vinyl acetate), poly(vinylidene chloride), and poly(vinyl chloride); diene polymers, such as 1,2-poly-1,3-butadiene, 1,4-poly-1,3-butadiene, polyisoprene, and polychloroprene; polystryrenes; copolymers of the foregoing, such as acrylonitrile-butadiene-styrene (ABS) copolymers; and the like. Preferably, first monocomponent fiber 26 is polyester, and most preferably, first monocomponent fiber 26 is poly(ethylene terephthalate) (PET). First monocomponent fiber 26 is important for the tensile strength of non-woven 12. Such fibers are commercially available from Wellman of Charlotte, N.C.

Denier, as used herein, refers to a weight-per-unit-length measure of a fiber, and it is a direct numbering system in which the lower numbers represent the finer sizes and the higher numbers represent the coarser sizes. Fibers of finer deniers feel softer, are more flexible and have more surface area, however, they are weaker in tensile strength than fibers of higher denier. Furthermore, fibers of lower denier yield a higher density, thinner non-woven. Conversely, higher fiber denier yields a coarser, lower density non-woven having a high loft.

The first monocomponent fiber 26 of the bottom layer may have any denier; and preferably, first monocomponent fiber 26 has a denier in the range of 2 to 10 denier per filament (dpf). Most preferably, first monocomponent fiber 26 has a denier in the range of 2.25 to 6 dpf to provide adequate strength while maintaining softness and flexibility, as well as high surface area for bonding.

The first monocomponent fiber 26 may have any cross section. Monocomponent fiber 26 may be a solid fiber, a hollow fiber, or a combination thereof.

The first monocomponent fiber 26 may have any orientation, i.e. machine direction (MD), or cross-machine direction (CD). Machine direction, as used herein, refers to the length of the non-woven in the direction in which it is produced, and the cross-machine direction is the width of the non-woven, i.e. a direction generally perpendicular to the machine direction orientation. Preferably, first monocomponent fiber 26 has a MD orientation.

The second monocomponent fiber 32 of the top layer may be a thermoplastic polymer, as described hereinabove. Preferably, second monocomponent fiber 32 is polyester and most preferably, second monocomponent fiber 32 is poly(ethylene terephthalate) (PET). Second monocomponent fiber 32 is important for the tensile strength of the loops of the loop component so that they withstand hook retraction. Such fibers are commercially available from Invista of Wichita, Kans.

Higher fiber denier, as mentioned hereinabove, yields a coarser non-woven loop material having a high loft. Loft, as described above, is important because a high loft non-woven is more open for hook component engagement and provides better resistance against loop compression. Therefore, optimum fiber denier, with regard to the second monocomponent fiber 32, is important in order to provide sufficient loop tensile strength, resistance to compression, adequate spacing among the loop fibers into which the hooks can enter and engage the loop fibers, and adequate softness and flexibility. The second monocomponent fiber 32 may have any denier; and preferably, second monocomponent fiber 26 has a denier in the range of 2 to 10 dpf. Most preferably, second monocomponent fiber 32 has a denier in the range of 2 to 9 dpf.

In the alternative, the second monocomponent fiber 32 may comprise a blend of two or more different monocomponent fibers. Preferably, 40 to 60 weight percent of the second monocomponent fiber 32 has a fiber denier in the range of 2 to 4 dpf, and the remaining balance thereof has a fiber denier in the range of 5 to 9 dpf. Most preferably, 40 to 60 weight percent of the second monocomponent fiber 32 has a fiber denier of 3 dpf, and the remaining balance thereof has a fiber denier of 6 dpf.

The second monocomponent fiber 32 may have any cross section. Monocomponent fiber 32 may be a solid fiber, a hollow fiber, or a multi-lobal fiber (e.g. trilobal fiber). Preferably, 40 to 60 weight percent of the second monocomponent fibers 32 are solid fibers or hollow fibers, and the remaining balance thereof are multi-lobal fibers (e.g. trilobal fibers).

The second monocomponent fiber 32 may have any orientation, i.e. machine direction (MD), or cross-machine direction (CD), as described hereinabove. Preferably, the second monocomponent fibers 32 have a MD orientation.

The first bicomponent fiber 28 of the bottom layer may be a bicomponent thermoplastic polymer fiber. Bicomponent thermoplastic polymer fibers, as used herein, refers to fibers which have been formed from at least two of the abovementioned thermoplastic polymers extruded from separate extruders but spun together to form one fiber. The polymers are arranged in substantially constantly positioned distinct zones across the cross-section of the bicomponent fibers and extend continuously along the length of the bicomponent fibers. The component polymers may be present in any desired ratio. The configuration of such a bicomponent fiber may be, for example, a core/sheath arrangement wherein one polymer is surrounded by another or a side-by-side arrangement. Preferably, the bicomponent thermoplastic polymer fibers have a core/sheath arrangement. The core and sheath components of the bicomponent thermoplastic polymer fiber may have any melting point temperatures. Preferably, sheath component of the bicomponent thermoplastic polymer has a lower melting point temperature than the core component of the bicomponent thermoplastic polymer. Most preferably, sheath component of the bicomponent thermoplastic polymer has a melting point temperature, which is 25 to 50° C. lower than the melting point temperature of the core component of the bicomponent thermoplastic polymer. Preferred examples of core/sheath arrangement bicomponent thermoplastic polymer fibers include polyolefin filaments, such as polyethylene terephthalate (PET)/polyethylene (PE), polyethylene terephthalate (PET)/copolymers of polyethylene terephthalate (CO-PET), polypropylene (PP)/polyethylene (PE), polyethylene terephthalate (PET)/polypropylene (PP), and polypropylene (PP)/polypropylene (PP). Most preferably, the bicomponent thermoplastic polymer, core/sheath arrangement, includes polyethylene terephthalate (PET) /polyethylene (PE), polyethylene terephthalate (PET)/polypropylene (PP), and polyethylene terephthalate (PET)/copolymers of polyethylene terephthalate (CO-PET).

The first bicomponent fiber 28 may have any denier. Preferably, first bicomponent fiber 28 has a denier in the range of 2 to 10 dpf in order to provide the optimum bonding surface necessary for strong interfiber bonding. More preferably, first bicomponent fiber 28 has a denier in the range of 3 to 6 dpf. Most preferably, first bicomponent fiber 28 has a denier of 4 dpf.

The first bicomponent fiber 28 of the top layer may have any orientation, i.e. machine direction (MD), or cross-machine direction (CD), as described hereinabove. Preferably, the first bicomponent fiber 28 has a MD orientation.

The second bicomponent fiber 34 may be a bicomponent thermoplastic polymer fiber. Bicomponent thermoplastic polymer fibers, as used herein, refers to fibers which have been formed from at least two of the abovementioned thermoplastic polymers extruded from separate extruders but spun together to form one fiber. The polymers are arranged in substantially constantly positioned distinct zones across the cross-section of the bicomponent fibers and extend continuously along the length of the bicomponent fibers. The component polymers may be present in any desired ratio. The configuration of such a bicomponent fiber may be, for example, a core/sheath arrangement wherein one polymer is surrounded by another or a side-by-side arrangement. Preferably, the bicomponent thermoplastic polymer fibers have a core/sheath arrangement. The core and sheath components of the bicomponent thermoplastic polymer fiber may have any melting point temperatures. Preferably, sheath component of the bicomponent thermoplastic polymer has a lower melting point temperature than the core component of the bicomponent thermoplastic polymer. Most preferably, sheath component of the bicomponent thermoplastic polymer has a melting point temperature, which is 25 to 50° C. lower than the melting point temperature of the core component of the bicomponent thermoplastic polymer. Preferred examples of core/sheath arrangement bicomponent thermoplastic polymer fibers include polyolefin filaments, such as polyethylene terephthalate (PET)/polyethylene (PE), polyethylene terephthalate (PET)/copolymers of polyethylene terephthalate (CO-PET), polypropylene (PP)/polyethylene (PE), polyethylene terephthalate (PET)/polypropylene (PP), and polypropylene (PP)/polypropylene (PP). Most preferably, the bicomponent thermoplastic polymer, core/sheath arrangement, includes polyethylene terephthalate (PET)/polyethylene (PE), polyethylene terephthalate (PET)/polypropylene (PP), and polyethylene terephthalate (PET)/copolymers of polyethylene terephthalate (CO-PET).

The second bicomponent fibers 34 may have any denier. Preferably, second bicomponent fiber 34 has a denier in the range of 2 to 10 dpf. More preferably, second bicomponent fiber 34 has a denier in the range of 3 to 6 dpf. Most preferably, second bicomponent fiber 34 has a denier of 4 dpf.

The second bicomponent fiber 34 may have any orientation, i.e. machine direction (MD), or cross-machine direction (CD), as described hereinabove. Preferably, the second bicomponent fiber 34 has a MD orientation.

Referring to FIGS. 2-4, in either bottom layer 16 or the top layer 18, the monocomponent fibers 26 and 32 do not bond to themselves and each other, but the bicomponent fibers 28 and 34 do bond to themselves as well as to monocomponent fibers 26 and 32; thus, there is no need for any binders. Binder, as used herein, refers to any polymeric material, which may be used to bind the fibers of a non-woven web.

Figure 9:
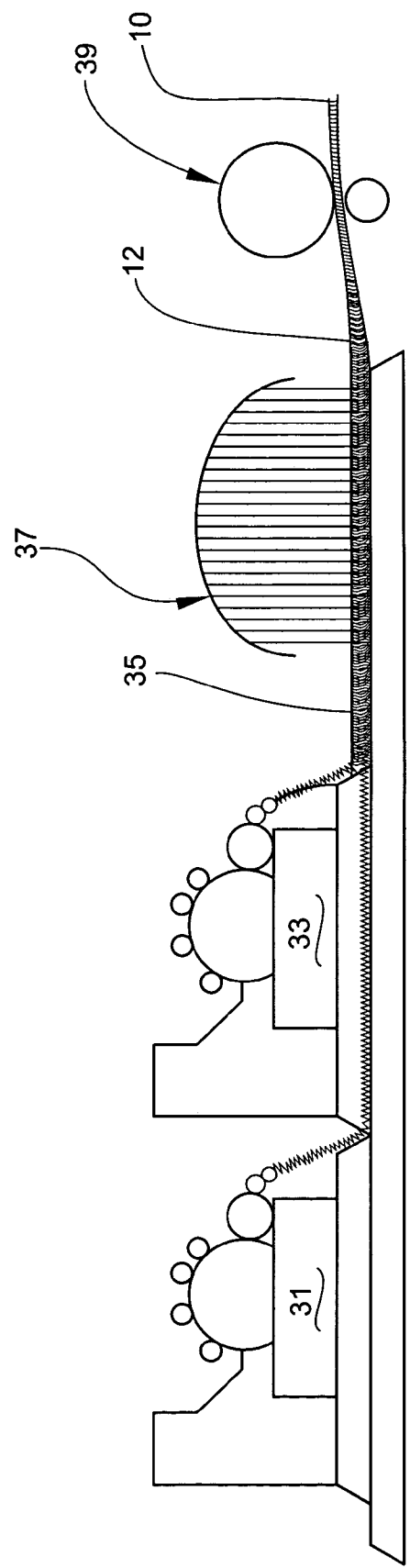
FIG. 9 is an schematic illustration of a manufacturing scheme for the loop component of the instant invention.

In the manufacturing of non-woven 12, bottom layer 16 or top layer 18 may be formed separately via a carding process, as illustrated in FIG. 9. Preferably, bottom layer 16 and top layer 18 are formed simultaneously via the carding process. In the alternative, bottom layer 16 or top layer 18 may be formed via airlaying.

In the carding process, staple fibers, which are usually purchased in bales, are separated via a picker. Next, the fibers are sent through a combing or carding unit, which further breaks apart and aligns the staple fibers in the machine direction to form a fibrous non-woven web. Once the web has been formed, it is then thermally interfiber bonded in a conventional manner to form interfiber bonded bottom layer 16 or interfiber bonded top layer 18. Conventional thermal bonding methods include, for example, infrared heat bonding 37 or hot-through-air bonding. Interfiber bonded bottom layer 16 and interfiber bonded top layer 18 may be formed separately as described above via carding process in two different steps. Preferably, interfiber bonded bottom layer 16 and interfiber bonded top layer 18 are formed simultaneously via two cards in a single step, as illustrated schematically in FIG. 9. First card 31 forms the non-woven web for the bottom layer 16, as described above, while second card 33 simultaneously forms non-woven web for top layer 18. Next, the non-woven web for top layer 18 is placed atop the non-woven web for bottom layer 16 to form a multilayer non-woven web 35, and then, the multi-layer non-woven web 35 is treated with infrared heat bonding 37 or hot-through-air bonding to form interfiber bonded bottom layer 16 and interfiber bonded top layer 18 simultaneously, and thereby forming non-woven 12. In the alternative, the webs for bottom layer 16 and top layer 18 may individually be treated with infrared heat bonding 37 or hot-through-air bonding to form interfiber bonded bottom layer 16, and interfiber bonded top layer 18. Subsequently, top layer 18 is placed atop bottom layer 16, and thereby forming non-woven 12.

The non-woven 12 may then be island bonded to itself thereby forming bonded area 20 and non-bonded area 22. In the alternative, non-woven 12 may be island bonded to a backing layer 14 thereby forming bonded area 20 and non-bonded area 22. The island bonding of non-woven 12 may further form polymer beads (not shown) along the edges of the bonded areas 20. These polymer beads along the edges of the bonded areas 20 are important because they improve the strength of the loops thereby providing stronger loops. The island bonding of non-woven 12, i.e. island bonding between interfiber bonded bottom layer 16 and interfiber bonded top layer 18, may be accomplished by different methods. Preferably, the island bonding of non-woven 12 is accomplished via thermal bonding. More preferably, the island bonding of non-woven 12 is accomplished via hot-roll calendering 39. Island bonding patterns and spacing will be discussed in greater detail below.

In infrared heat bonding, the non-woven web is subjected to infrared heat while in hot-through-air bonding, hot air is passed through the non-woven web. In either method, sufficient heat is applied to soften or melt the sheath of the bicomponent fibers of the non-woven web enabling interfiber bonding between adjacent fibers.

Airlaying is a well know process by which fibrous non-woven webs can be formed. In airlaying process, bundles of small fibers are separated and entrained in an air supply and then deposited onto a forming screen, usually with the assistance of a vacuum supply. The randomly deposited fibers then can be bonded to one another using a conventional manner, as described above.

Hot-roll calendering refers to a bonding process via application of heat and pressure wherein non-woven 12 is passed between a heated embossed roll and a smooth roll under pressure thereby forming a bonded area 20 therebetween, as shown in FIG. 2. In the alternative, non-woven 12 and backing layer 14 are co-fed through a calender having at least two rolls, i.e. a smooth roll and a heated embossed roll with desired non-bonding patterns thereby forming a bonded area 20.

Island bonding patterns and spacing will be discussed hereinafter. The bonded area 20 may cover any portion of the non-woven 12. Preferably, the bonded area 20 covers an area in the range of 25 to 60 percent based on the total area of the non-woven 12. Most preferably, the bonded area 20 covers an area in the range of 33 to 55 percent based on the total area of the non-woven 12. Bonded area 20 is important because sufficient bonding area provides for a strongly bonded non-woven material 12. Furthermore, the bonded area 20 secures the loop fibers to the non-woven 12 structure, so that the loop fibers do not easily pull free from the non-woven structure 12 upon the retraction of the hooks therefrom.

Figure 5A:
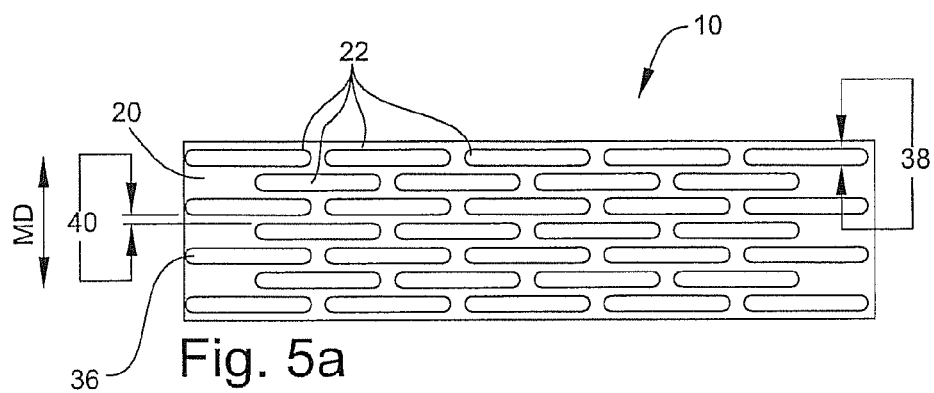
FIGS. 5a, b, c, and d are schematic illustrations of different shapes of non-bonded area of the loop component (MD is top to bottom)
Figure 5B:
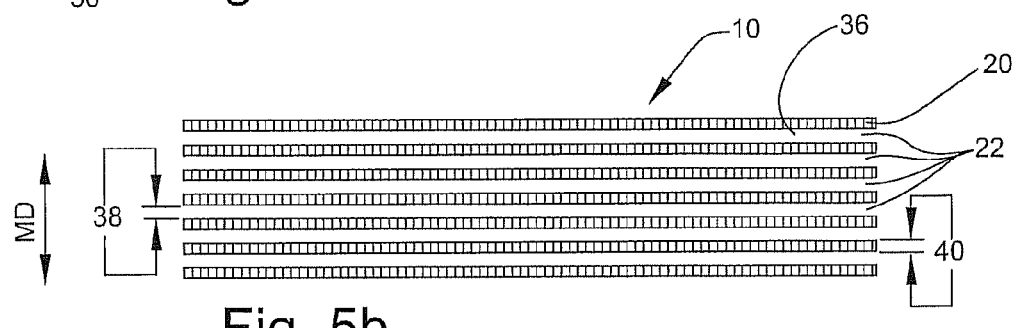
Figure 5C:
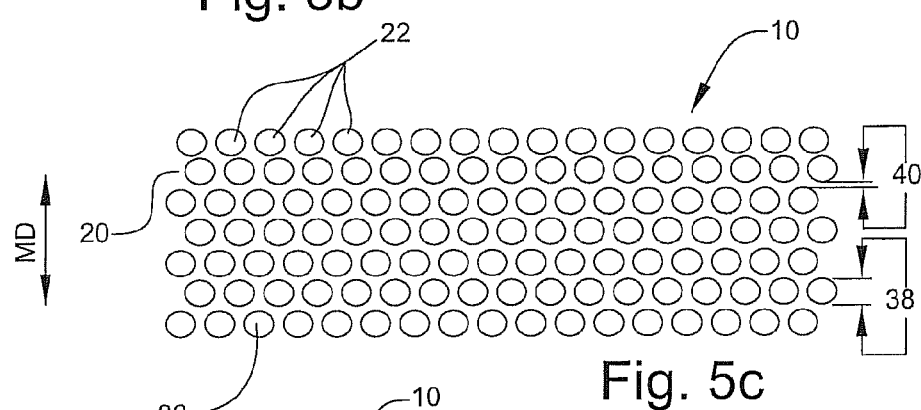
Figure 5D:
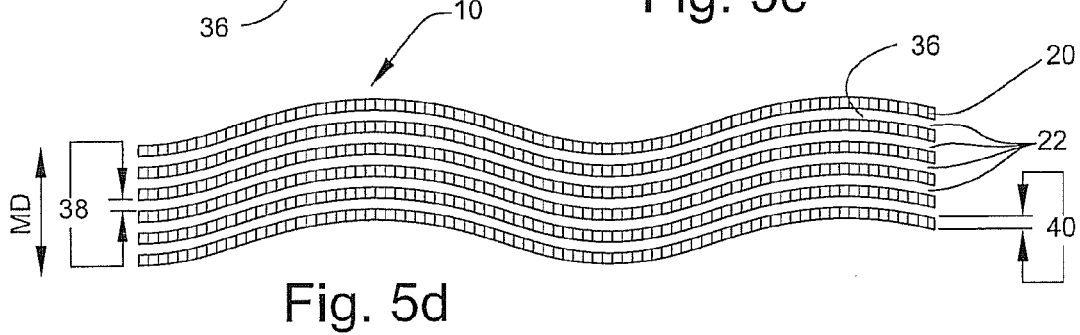

Referring to FIGS. 5a, b, c and d, the non-bonded area 22 is defined by the bonded area 20, and as used herein, refers to the regions available for hook engagement, i.e. loop fibers. The non-bonded area 22 may cover any portion of the non-woven 12. Preferably, the non-bonded area 22 covers an area in the range of 45 to 67 percent based on the total area of the non-woven 12. The non-bonded area 22 comprises a plurality of non-bonded islands 36. Non-bonded islands, as used herein, refers to isolated non-bonded regions surrounded entirely by the bonded area 20. Each non-bonded island 36 has a non-bonding pattern selected from the group consisting of slots, bars, squares, circles, diamonds, sinusoidal wave patterns, combinations thereof, and the like. Non-bonded islands 36 may have any orientation, i.e. machine direction or cross-machine direction. Preferably, non-bonded islands 36 have a machine direction orientation. Each non-bonded island 36 may have any MD width 38. The MD width 38 of each non-bonded island 36 is important because the MD width 38 of the non-bonded islands 36 determines the length of each individual loop fibers. The length of each individual loop fiber is important because it directly affects the fastening performance, i.e. peel strength, and shear strength, of the loop component 10, as shown in Tables I and II. The greater the MD width 38 of each non-bonded island 36, the greater the number of hooks capable of engaging the loop fibers; consequently, there is a greater possibility that loop fibers break and/or pull free from bonded area 20, and generate fuzz. In addition, if an excessive amount of loop fibers break and/or pull free from bonded area 20, then the peel performance will be negatively affected. Preferably, each non-bonded island 36 has a MD width 38 in the range about 1.5 to 3 mm.

Non-bonded islands 36 may be spaced apart from each other in any direction. Preferably, non-bonded islands 36 are spaced apart from each other in a machine direction. Non-bonded islands 36 may be spaced apart from each other any distance 40 in MD. Preferably, the distance 40 is in the range of 1 to 2 mm. The distance 40 is important because it ensures strong bonding foundation for a loop component 10.

Referring to FIG. 6, there is shown a preferred embodiment of a hook and loop fastener device 42, which includes the loop component 10 of the instant invention. The fastener device 42 includes a loop component 10, as described hereinabove, and a hook component 44. Referring to FIG. 7, the hook component 44 comprises a base 46, a plurality of upstanding engaging elements 48 extending from one surface of the base 46. Each upstanding engaging element includes a stem 50 and a hook member 52. Upstanding engaging elements 48 may have any shape. Preferably, upstanding engaging elements 48 have a shape selected from the group consisting of J-shape, T-shape, mushroom shape, and combinations thereof.

In operation, referring to FIGS. 6 and 7, the hook component 44 and the loop component 10 are pressed face-to-face against each other. Thus, the hook members 52 are entangled by the loop fibers of the non-woven 12. The non-woven 12 provides space for the upstanding engaging elements 48, and particularly, for hook members 52 to occupy when the fastener device 42 is closed. The engagement therebetween the hook component 44 and the loop component 10 provides a connection which resists the forces that may be exerted on the fastener device 42.

Figure 8:
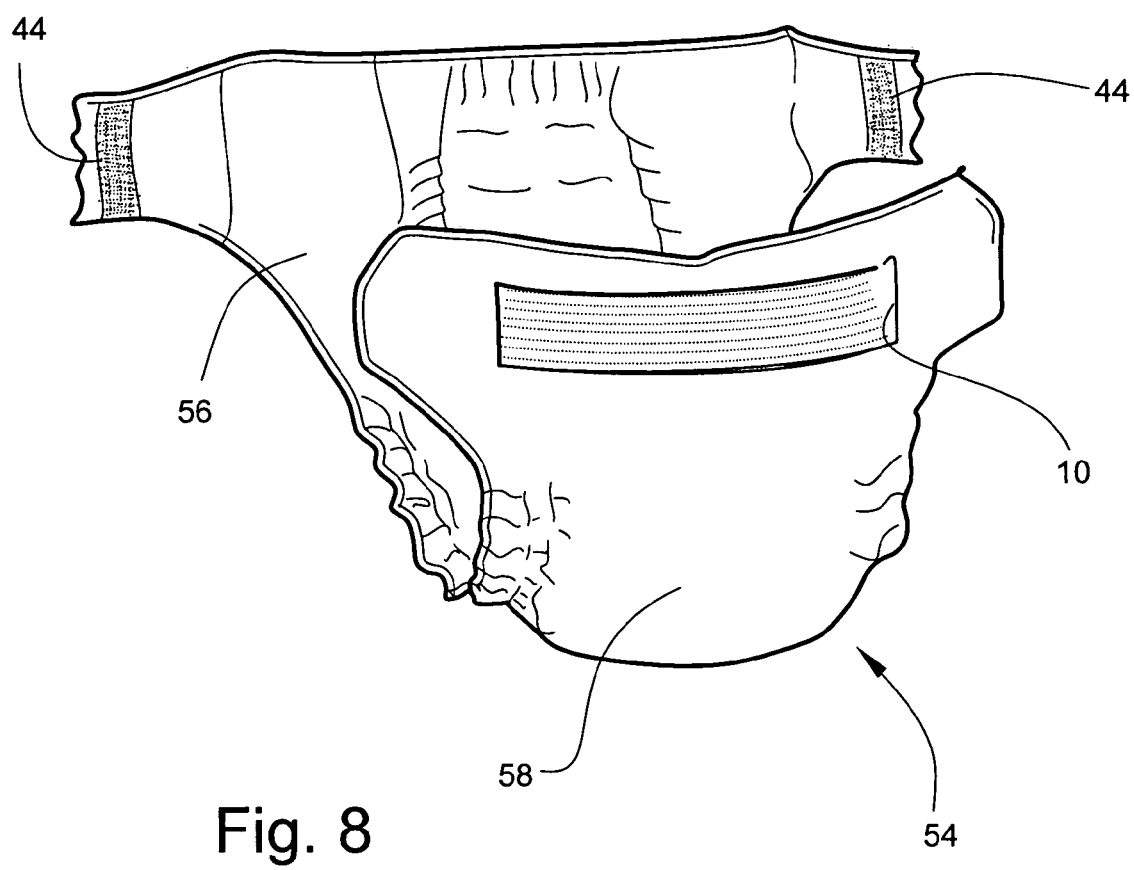
FIG. 8 is a perspective view of a disposable diaper including the loop component of the instant invention.

The hook and loop fastener device 42 is especially useful as a fastening device for disposable articles, particularly, disposable absorbent articles such as diapers. Preferably, the hook and loop fastener device 42 is utilized as a fastening device in disposable diapers 54, as shown in FIG. 8.

A disposable diaper 54 includes a body liner 56, an outer cover 58, an absorbent structure (not shown) disposed therebetween the bodyside liner 56 and the outer cover 58, and a fastening device. Preferably, the fastening device is a hook and loop fastener device 42, and more preferably, the fastening device 42 includes loop component 10, as described hereinabove. The loop component 10 may be affixed to the outer cover 58 via glue bonding process or ultrasonic bonding process.

The present invention further provides a method of preparing a loop component 10 suitable for use in a hook and loop device 42. First, bottom layer 16, as described hereinabove, is provided, and then, top layer 18, as described hereinabove, is provided. Top layer 18 is placed atop of bottom a layer 16, thereby forming binder-free non-woven 12. Backing layer 14 may be provided. Backing layer 14 may then be thermally island bonded to non-woven 12 to form bonded area 20 and non-bonded area 22. In the alternative, where backing layer 14 is not provided, non-woven 12 may be thermally island bonded to itself to form bonded area 20 and non-bonded area 22.

EXAMPLE I

In the first test, ten different loop component samples, i.e. samples 1-10, as described hereinbelow in detail, were prepared, and tested for fastening performance, i.e. peel strength. The results of the aforementioned test are shown below in Table I. Each of the ten loop component samples, i.e. samples 1-10, comprised a non-woven with total basis weight of 35.6 g/m$^2$, and each said non-woven had a top layer and bottom layer. Each top layer had a total basis weight of 26 g/m$^2$, and furthermore, each said top layer further comprised 4 denier per filament (dpf) PET/CoPET concentric core bicomponent fibers with a basis weight of 5.25 g/m$^2$; 3 dpf round PET staple fibers with a basis weight of 10.5 g/m$^2$; and 6 dpf trilobal PET staple fiber with a basis weight of 10.5 g/m$^2$ Each bottom layer had a total basis weight of 9.6 g/m$^2$, and furthermore, each said bottom layer comprised a 4 dpf PET/CoPET concentric core bicomponent fiber with a basis weight of 7.2 g/m$^2$; and 2.25 dpf round PET staple fiber with a basis weight of 2.4 g/m$^2$. Each said non-woven sample was island bonded at the same temperature and pressure thereby forming bar patterns. MD width 38 ranged from 1.5 to 3.5 mm while the MD distance 40 ranged from 1 to 2 mm. Said samples were tested using a commercially available hook known as CS600 from 3M Company. CS600 has 1700 hooks per inch$^2$, and has a width of 15 mm.

The peel strength, as described hereinbelow, was determined, and subsequently, samples were observed for the amount fuzz formation.

The 180° peel strength test involves attaching a hook component to a loop component of a hook and loop fastening system and then peeling the hook component from the loop component at a 180° angle. The maximum load needed to disengage the two components is recorded in newtons. As shown in Table I, peel strength results indicate that such peel strength results greater than 3 newtons are considered acceptable; however, higher peel strength is preferred. In this first test, while the peel strength results and the amount of fuzz formation of the samples Nos. 1 to 8 are preferred, the peel strength results and the amount of fuzz formation of the samples Nos. 1 to 6 are more preferred. Furthermore, the peel strength results, as shown in Table I, indicate that a non-woven having a total non-bonded area of 46 to 67 percent based on the total area of the non-woven 12, a MD distance 40 in the range of 1 to 2 mm, and a MD width 38 in the range of 1.5 to 3 mm would yield preferred peel performance and fuzz formation.

TABLE I

| Sample No. | MD Width 38, mm | MD Distance 40, mm | % Non-bonded Area | 180° Peel, Peek Force newtons (average) | Results |
|---|---|---|---|---|---|
| 1 | 1.5 | 1.75 | 46.2% | 3.5 | low fuzz |
| 2 | 1.5 | 1 | 60.0% | 3.5 | low fuzz |
| 3 | 2 | 2 | 50.0% | 4.2 | low fuzz |
| 4 | 2 | 1.5 | 57.1% | 4.5 | low fuzz |
| 5 | 2 | 1 | 66.7% | 4.6 | low fuzz |
| 6 | 2.25 | 1.75 | 56.3% | 4.6 | low fuzz |
| 7 | 3 | 2 | 60.0% | 4.9 | low fuzz |
| 8 | 3 | 1.5 | 66.7% | 5.8 | low to medium fuzz |
| 9 | 3 | 1 | 75.0% | 6.0 | high fuzz |
| 10 | 3.5 | 1 | 77.8% | 6.0 | high fuzz |

EXAMPLE II

In a second test, ten different loop component samples, i.e. samples 11-20, as described hereinbelow in detail, were prepared, and tested for fastening performance, i.e. peel strength. The results of the aforementioned test are shown below in Table II. Each of the ten loop component samples, i.e. samples 11-20, comprised a non-woven with total basis weight of 35.9 g/m$^2$, and each said non-woven had a top layer and bottom layer. Each top layer had a total basis weight of 21.5 g/m$^2$, and furthermore, each said top layer further comprised 4 denier per filament (dpf) PET/PP concentric core bicomponent fibers with a basis weight of 4.3 g/m$^2$; 3 dpf round PET staple fibers with a basis weight of 8.6 g/m$^2$; and 6 dpf trilobal PET staple fiber with a basis weight of 8.6 g/m$^2$. Each bottom layer had a total basis weight of 14.4 g/m$^2$, and furthermore, each said bottom layer comprised a 4 dpf PET/PP concentric core bicomponent fiber with a basis weight of 12.9 g/m$^2$; and 2.25 dpf round PET staple fiber with a basis weight of 1.4 g/m$^2$. Each said non-woven sample was island bonded at the same temperature and pressure thereby forming bar patterns. The island bonding further formed polymer beads along the edges of the bonded areas. MD width 38 ranged from 1.5 to 3.5 mm while the MD distance 40 ranged from 1 to 2 mm. Said samples were tested using an experimental hook, 731B, from Aplix S.A. The 731B is a "J" shaped hook having about 1150 hooks per inch$^2$. The 731B has a head height from the base of about 0.13 mm, and a tape width of 15 mm.

The peel strength, as described hereinabove, was determined, and subsequently, samples were observed for the amount fuzz formation.

As shown in Table II, peel strength results indicate that such peel strength results greater than 3 newtons are considered acceptable; however, higher peel strength is preferred. In this second test, while the peel strength results and the amount of fuzz formation of the samples Nos. 11 to 18 are preferred, the peel strength results and the amount of fuzz formation of the samples Nos. 11 to 16 are most preferred. Furthermore, the peel strength results, as shown in Table II, indicate that a non-woven having a total non-bonded area of 46 to 67 percent based on the total area of the non-woven 12, a MD distance 40 in the range of 1 to 2 mm, and a MD width 38 in the range of 1.5 to 3 mm would yield the most preferred peel performance and fuzz formation.

TABLE II

| Sample No. | MD Width 38, mm | MD Distance 40, mm | % Non-bonded Area | 180° Peel, Peek Force newtons (average) | Results |
|---|---|---|---|---|---|
| 11 | 1.5 | 1.75 | 46.2% | 3.0 | low fuzz |
| 12 | 1.5 | 1 | 60.0% | 3.0 | low fuzz |
| 13 | 2 | 2 | 50.0% | 3.7 | low fuzz |
| 14 | 2 | 1.5 | 57.1% | 4.0 | low fuzz |
| 15 | 2 | 1 | 66.7% | 3.7 | low fuzz |
| 16 | 2.25 | 1.75 | 56.3% | 3.8 | low fuzz |
| 17 | 3 | 2 | 60.0% | 4.4 | low fuzz |
| 18 | 3 | 1.5 | 66.7% | 4.3 | medium fuzz |
| 19 | 3 | 1 | 75.0% | 4.3 | high fuzz |
| 20 | 3.5 | 1 | 77.8% | 6.0 | high fuzz |

The present invention may be embodied in other forms without departing from the spirit and the essential attributes thereof, and, accordingly, reference should be made to the appended claims, rather than to the foregoing specification, as indicating the scope of the invention.

We claim:

1. A loop component for a hook and loop fastener device comprising:
a binder-free thermally bonded non-woven material having a bottom layer and a top layer, said bottom layer comprising a first bicomponent fiber and a first monocomponent fiber, wherein said first bicomponent fiber comprising a majority of said bottom layer based on total weight of said bottom layer and said first monocomponent fiber being the balance thereof, said top layer comprising a second bicomponent fiber, and a second monocomponent fiber, said second monocomponent fiber comprising a majority of said top layer based on total weight of said top layer and said second bicomponent fiber being the balance thereof
wherein said non-woven being island-bonded to itself thereby forming a bonded area, said bonded area further defining a non-bonded area.

2. The loop component according to claim 1, wherein said bottom layer being interfiber bonded and said top layer being interfiber bonded.

3. The loop component according to claim 2, wherein said interfiber bonding in each said bottom layer and said top layer being accomplished via a thermally bonding process selected form the group consisting of hot-through-air bonding and infrared heat bonding.

4. The loop component according to claim 1, wherein said bonded area including polymer beads along the edges of said bonded area.

5. The loop component according to claim 1, wherein said loop component further comprising a backing layer.

6. The loop component according to claim 5, wherein said backing layer being a polymeric film.

7. The loop component according to claim 6, wherein said polymeric film being made of a material selected from the group consisting of polyester, polyethylene, polypropylene, and combinations thereof.

8. The loop component according to claim 6, wherein said film having a basis weight in the range of 10 to 30 g/m$^2$ and a thickness in the range of 9 to 28µ.

9. The loop component according to claim 1, wherein said non-woven being island-bonded to itself via hot-roll calendering process.

10. The loop component according to claim 1, wherein said non-bonded area comprises 46 to 67% of said non-woven based on the total area of said non-woven.

11. The loop component according to claim 1, wherein said non-bonded area comprising a plurality of non-bonded islands, each said non-bonded island having a non-bonding pattern selected from the group consisting of slots, bars, squares, circles, diamonds, sinusoidal wave patterns, combinations thereof, and the like.

12. The loop component according to claim 11, wherein each said non-bonded island having a width in a machine direction in the range of 1.5 to 3 mm.

13. The loop component according to claim 11, wherein each said non-bonded island being spaced apart from each other a distance in range of 1 to 2 mm in a machine direction.

14. The loop component according to claim 1, wherein said non-woven material having a basis weight in the range of 20 to 50 g/m$^2$.

15. The loop component according to claim 1, wherein said non-woven material having a basis weight in the range of 30 to 37 g/m$^2$.

16. The loop component according to claim 1, wherein said non-woven material having a thickness in the range of 1.0 to 2.3 mm (40 to 90 mils).

17. The loop component according to claim 1, wherein each said first bicomponent fiber and said second bicomponent fiber comprising polyethylene terephthalate and a copolymer of polyethylene terephthalate (PET/CO-PET) or polyethylene terephthalate and polypropylene (PET/PP).

18. The loop component according to claim 1, wherein said first bicomponent fiber comprising 60 to 99% of said bottom layer based on total weight of said bottom layer and said first monocomponent fiber comprising 1 to 40% of said bottom layer based on total weight of said bottom layer.

19. The loop component according to claim 1, wherein said first bicomponent fiber comprising about 90% of said bottom layer based on total weight of said bottom layer and said first monocomponent fiber comprising 10% of said bottom layer based on total weight of said bottom layer.

20. The loop component according to claim 1, wherein said second bicomponent fiber comprising 1 to 40% of said top layer based on total weight of said top layer and said second monocomponent fiber comprising 60 to 99% of said top layer based on total weight of said top layer.

21. The loop component according to claim 1, wherein said second bicomponent fiber comprising 20% of said top layer based on total weight of said top layer, and said second monocomponent fiber comprising 80% of said top layer based on total weight of said top layer.

22. The loop component according to claim 1, wherein each said first monocomponent fiber and said second monocomponent fiber comprising polyethylene terephthalate.

23. The loop component according to claim 1, wherein each said bicomponent fibers and each said monocomponent fibers having a fiber denier of 2 to 10 denier per filament (dpf).

24. The loop component according to claim 1, wherein 40 to 60 weight percent of said second monocomponent fiber having a fiber denier in the range of 2 to 4 denier per filament, and the remaining balance thereof having a fiber denier in the range of 5 to 9 denier per filament.

25. A disposable absorbent article comprising:
a bodyside liner;
an outer cover;
an absorbent structure disposed therebetween said bodyside liner and said outer cover; and
a loop component comprising;
a binder-free thermally bonded non-woven material having a bottom layer and a top layer, said bottom layer comprising a first bicomponent fiber and a first monocomponent fiber, wherein said first bicomponent fiber comprising a majority of said bottom layer based on total weight of said bottom layer and said first monocomponent fiber being the balance thereof, said top layer comprising a second bicomponent fiber, and a second monocomponent fiber, said second monocomponent fiber comprising a majority of said top layer based on total weight of said top layer and said second bicomponent fiber being the balance thereof, said loop component being affixed to said outer cover; and a hook component affixed to said outer cover.

26. A disposable absorbent article comprising:
a bodyside liner;
an outer cover;
an absorbent structure disposed therebetween said bodyside liner and said outer cover; and
a loop component consisting of;
 a thermally bonded non-woven material having a bottom layer and a top layer, said bottom layer comprising a first bicomponent fiber and a first monocomponent fiber, wherein said first bicomponent fiber comprising a majority of said bottom layer based on total weight of said bottom layer and said first monocomponent fiber being the balance thereof, said top layer comprising a second bicomponent fiber, and a second monocomponent fiber, said second monocomponent fiber comprising a majority of said top layer based on total weight of said top layer and said second bicomponent fiber being the balance thereof, said loop component being affixed to said outer cover; and
a hook component affixed to said outer cover.

* * * * *